United States Patent [19]

Nadelson

[11] 4,006,248
[45] Feb. 1, 1977

[54] ALKYL-p-PIVALOYLBEN-ZYLAMINOMETHYL-BENZOPHENONES

[75] Inventor: Jeffrey Nadelson, Lake Parsippany, N.J.

[73] Assignee: Sandoz, Inc., E. Hanover, N.J.

[22] Filed: Aug. 21, 1975

[21] Appl. No.: 606,459

[52] U.S. Cl. .......................... 424/316; 260/501.18; 260/570 R; 260/591; 424/330
[51] Int. Cl.² ...................... A01N 9/20; C07C 97/10
[58] Field of Search .................. 260/570 R, 501.18; 424/316, 330

[56] References Cited

UNITED STATES PATENTS

| | | | |
|---|---|---|---|
| 3,123,643 | 3/1964 | Palopoli et al. | 260/570 |
| 3,380,961 | 4/1968 | Dressler et al. | 260/570 X |
| 3,497,508 | 2/1970 | Houlihan | 260/570 X |
| 3,639,481 | 2/1972 | Innes | 260/570 X |

*Primary Examiner*—Robert V. Hines
*Attorney, Agent, or Firm*—Gerald D. Sharkin; Robert S. Honor

[57] ABSTRACT

Alkyl-p-pivaloylbenzylaminomethyl-benzophenones, e.g., 4-{[methyl(p-pivaloylbenzyl)amino]methyl}benzophenone, are prepared by treating a corresponding 4-benzoyl-N-alkyl-benzylamine with a corresponding α-halo-p-pivaloyl toluene and are useful as hypolipidemic agents.

9 Claims, No Drawings

ALKYL-p-PIVALOYLBENZYLAMINOMETHYL-BENZOPHENONES

This invention relates to alkyl-p-pivaloylbenzylaminomethyl-benzophenones which exhibit hypolipidemic activity. In particular, it relates to alkyl-p-pivaloylbenzylaminomethyl-benzophenones, pharmaceutically acceptable salts thereof and to their preparation.

The compounds of this invention may be represented by the following structural formula

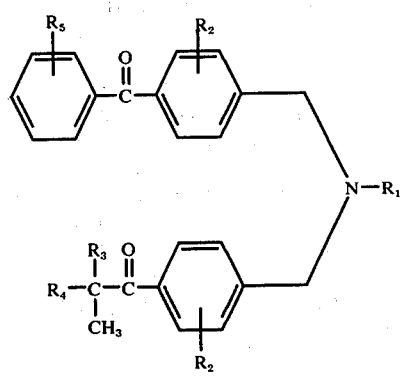

where
$R_1$ represents lower alkyl, i.e. alkyl having 1 to 4 carbon atoms, e.g. methyl, ethyl and the like, and
$R_2$ each independently represent hydrogen or halo having an atomic weight of about 19 to 36, i.e. fluoro or chloro,
$R_3$ and $R_4$ each independently represent lower alkyl having 1 to 2 carbon atoms, i.e. methyl and ethyl, and
$R_5$ represents hydrogen or halo as defined above.

The compounds of formula (I) are prepared according to the following reaction scheme:

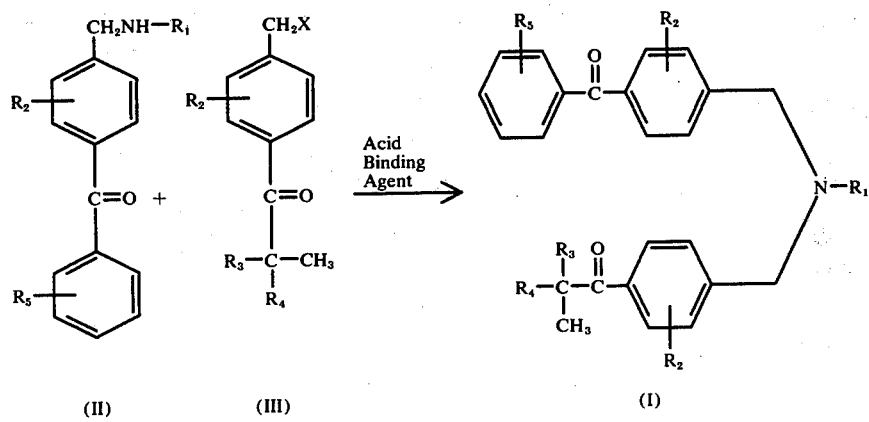

where
X represents chlorine or bromine, and
$R_1$, $R_2$, $R_3$, $R_4$, and $R_5$ are as defined above.

The compounds of formula (I) are prepared by treating a compound of the formula (II) with a compound of the formula (III) in the presence of an acid binding agent such as pyridine, triethylamine, N,N-diisopropyl ethyl amine and the like, preferably N,N-diisoprophyl ethyl amine in the presence of an inert organic solvent. Although the particular solvent employed is not critical, it is preferred that an aromatic hydrocabon such as benzene, toluene and the like, or a halogenated hydrocarbon such as methylenedichloride, chloroform, and the like, be employed, preferably toluene. The temperature of the reaction is not critical, but it is preferred that the reaction be carried out at a temperature of from about 25° to 150° C., preferably from about 80° to 120° C. The reaction may be run from about 3 to 24 hours, preferably from about 16 to 20 hours. The product is recovered using conventional techniques, e.g. column chromatography followed by filtration.

The compounds of formula (II) are prepared according to the following reaction scheme:

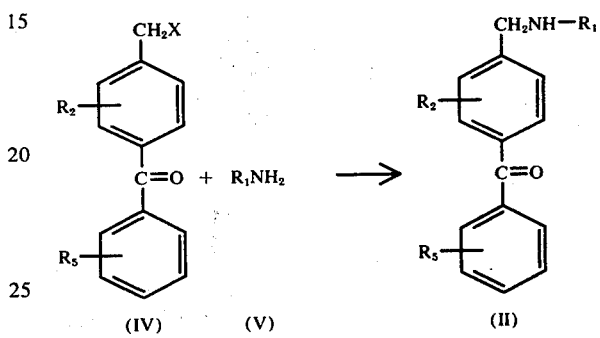

where
X is chlorine or bromine, and
$R_1$, $R_2$ and $R_5$ are as defined above.

The compounds of formula (II) are prepared by treating a compound of the formula (IV) with a compound of the formula (V) in the presence of an inert organic solvent. Although the particular solvent employed is not critical, it is preferred that the reaction be carried out in the presence of an aromatic hydrocarbon such as benzene, toluene and the like or a halogenated hydrocarbon, such as methylenedichloride, chloroform and the like, preferably benzene. The temperature of the reaction is not critical, but it is preferred that the reaction be run at a temperature of from about 10° to 100° C., preferably from about 25° to 40° C. The reaction is run from about 30 minutes to 10 hours, preferably from 4 to 6 hours. The product is recovered by column chromatography.

The compounds of formula (IV) are prepared according to the following reaction scheme:

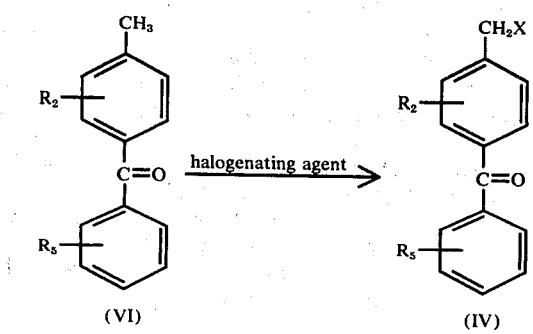

(VI)   (IV)

where X, R₂ and R₅ are defined above.

The compounds of formula (IV) are prepared by treating a compound of formula (VI) with a halogenating agent in the presence of an inert organic solvent and free radical initiator. The halogenating agent which can be used in bromine, N-bromosuccinimide, N-bromo phthalimide, N-bromoacetamide, chlorine, N-chlorosuccinimide and the like. The particular agent used is not critical, but N-bromosuccinimide is preferred. In the preferred process, the free radical initiator used is an organic peroxide, especially benzoyl peroxide. The reaction can also be carried out under ultraviolet light. Although the particular solvent used is not critical, the preferred solvents are the halogenated hydrocarbons such as methylenedichloride, chloroform, carbon tetrachloride and the like, although the aromatic hydrocarbons such as benzene, toluene and the like can also be employed. The temperature of the reaction is not critical, but reflux temperature of the solvent is preferred. The reaction is run for about 12 to 48 hours; preferably about 18 to 25 hours. The product is recovered by conventional techniques, e.g., crystallization.

Many of the compounds of formulae (III), (V) and (VI) are known and may be prepared by methods described in the literature. The compounds of formulae (III), (V) and (VI) not specifically described many be prepared by analogous methods from known starting materials.

The compounds of formula (I) are useful because they possess pharmaceutical activity in animals as hypolipidemic agents, as indicated by the fall in cholesterol and triglyceride levels in male albino Wistar rats weighing 110–130 g. initially. The rats are maintained on drug-free laboratory chow diet for seven days and then divided into groups of 8 to 10 animals. Each group with the exception of the control is then given orally 120 milligrams per kilogram of body weight per diem of the compound for six days. At the end of this period, the animals are anesthetized with sodium hexobarbital and bled from the carotid arteries. Serum or plasma samples are collected, and 1.0 ml. samples of the serum are added to 9.0 redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, (345–347) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g. a sterile injectable aqueous solution. The dosage will vary depending upon the mode of administration utilized and the particular compound employed.

The compound of formula (I) may be similarly administered in the form of their non-toxic pharmactutically acceptable salts. Such salts possess the same order of activity as the free base and are readily prepared by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

It is to be noted that the salt may also be converted to the base by conventional techniques, e.g. treatment with alkali metal hydroxide followed by extraction with inert organic solvent, and are also included within the scope of the invention.

The hypolipidemic effective dosage of these active compounds in the alleviation of lipidemia may vary depending on the particular compound employed and the severity of the condition being treated. However, in general, satisfactory results are obtained when the compounds of formula (I) are administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 1500 milligrams. Dosage forms suitable for internal use comprise from about 75.0 to about 750 milligrams of the active compound in intimate admixture with a solid or liquid pharmactutically acceptable carrier or diluent.

A representative formulation suitable for oral administration 2 to 4 times a day for the treatment of lipidemia is a capsule prepared by standard encapsulating techniques which contains the following:

| Ingredients | Weight (mg.) |
| --- | --- |
| 4-{[methyl(p-pivaloylbenzyl)amino]methyl}benzophenone | 150 |
| inert solid diluent (starch, lactose, kaolin) | 300 |

A preferred aspect of this invention concerns compounds (I) wherein R₁ represents methyl, R₂ and R₅ represent hydrogen and R₃ and R₄ represent methyl.

EXAMPLE 1

α-bromo-4-benzoyl-toluene

A mixture of 19.6 g. (0.1 mole) 4-methyl benzophenone 17.8 g. (0.1 mole) N-bromosuccinimide, 0.4 g. (0.0016 mole) benzoyl peroxide and 200 ml. carbon tetrachloride is refluxed for 18 hours. The mixture is then cooled and filtered, and the resulting solid is suspended in water, filtered and washed with water. The wet solid is dissolved in methylene chloride, washed with water and brine, dried over anhydrous magnesium sulfate and evaporated to give α-bromo-4-benzoyl toluene, m.p. 104° to 109° C.

Following the above procedure and using in place of 4-methyl benzophenone an equivalent amount of
a. 2,2'-dichloro-4-methyl benzophenone, or
b. 2,2'-difluoro-4-methyl benzophenone,
there is obtained
a. α-bromo-2-chloro-4-(2-chlorobenzoyl)-toluene, or
b. α-bromo-2-fluoro-4-(2-fluorobenzoyl)-toluene, respectively.

EXAMPLE 2

4-benzoyl-N-methyl benzyl amine

A solution of 12.0 g. (0.379 mole) anhydrous methyl amine in 150 ml. benzene is treated dropwise with 34.8 g. (0.127 mole) α-bromo-p-benzoyl toluene in 300 ml. benzene for about 30 minutes. The resulting mixture is stirred for 4 hours at room temperature and the solvent removed in vacuo. The resulting residue is dissolved in ether and washed with water. The ether layer is then extracted three times with 2N hydrochloric acid and the acidic solution made basic by the addition of potassium hydroxide and extracted with ether. The ether layer is washed with water, dried over anhydrous magnesium sulfate and evaporated in vacuo. The residue is then chromatographed on silica gel to yield 4-benzoyl N-methyl benzyl amine (identified by spectral analysis).

Following the above procedure and using in place of α-bromo-p-benzoyl toluene an equivalent amount of
a. α-bromo-2-chloro-4-(2-chlorobenzoyl)-toluene, or
b. α-bromo-fluoro-4-(2-fluorobenzoyl)-toluene,
there is obtained
a. 2-chloro-4-(2-chlorobenzoyl)-N-methyl-benzyl amine, or
b. 2-fluoro-4-(2-fluorobenzyl)-N-methyl-benzyl amine, respectively.

EXAMPLE 3

4-{[methyl (p-pivaloylbenzyl)amino]methyl}benzophenone

A solution of 6.0 g. (0.027 mole) 4-benzoyl-N-methyl benzyl amine and 3.9 g. (0.030 mole) N,N-diisopropyl ethyl amine in 100 ml. toluene is treated by the dropwise addition of 6.9 g. (0.027 mole) α-bromo-p-pivaloyl toluene in 50 ml. toluene for about 20 minutes. The mixture is refluxed overnight, cooled and extracted with water. The organic layer is extracted twice with 2N hydrochloric acid and the aqueous acid extracts made basic by the addition of potassium hydroxide and extracted with ether. The ether layer is washed with water, dried over magnesium sulfate and evaporated in vacuo. The residue is chromatographed on silica gel and the major fraction dissolved in ether containing a small amount of ethanol and treated with gaseous hydrochloric acid. The solid is filtered to give 4-{[methyl(p-pivaloylbenzyl) amino]methyl}benzophenone hydrochloride, m.p. 186.5° to 187.5° C.

Following the above procedure and using in place of 4-benzoyl-N-methyl-benzyl amine an equivalent amount of a. 2-chloro-4-(2-chlorobenzoyl)-N-methyl-benzyl amine, or
b. 2-fluoro-4-(2-fluorobenzoyl)-N-methyl-benzyl amine, and using in place of α-bromo-p-pivaloyl toluene an equivalent amount of
a'. α-bromo-2-chloro-4-pivaloyl toluene, or
b'. α-bromo-2-fluoro-4-pivaloyl toluene,
there is obtained
a. 4-{[methyl(3-chloro-4-pivaloylbenzyl)amino]methyl}2',3-dichlorobenzophenone hydrochloride, or
b. 4-{[methyl(3-fluoro-4-pivaloylbenzyl) amino]methyl}2',3-difluorobenzophenone hydrochloride, respectively.

The 4-{[methyl(p-pivaloylbenzyl)amino]methyl} benzophenone of this example is an effective hypolipidemic agent when orally administered to an animal suffering from lipidemia at a dosage of 150 mg. four times per day. What is claimed is:

1. A compound of the formula

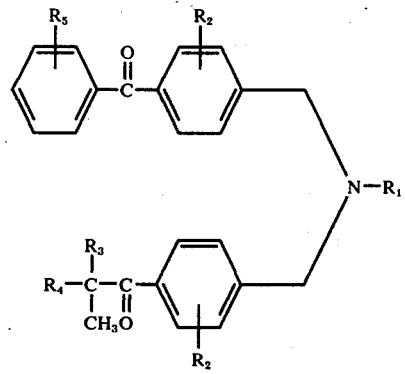

where
$R_1$ represents lower alkyl having 1 to 4 carbons atoms, and
$R_2$ each independently, represent hydrogen or halo having an atomic weight of about 19 to 36, and
$R_3$ and $R_4$ each independently represent lower alkyl having 1 to 2 cabon atoms, and
$R_5$ represents hydrogen or halo as defined above,
or a pharmaceutically acceptable salt thereof.

2. A compound of the formula

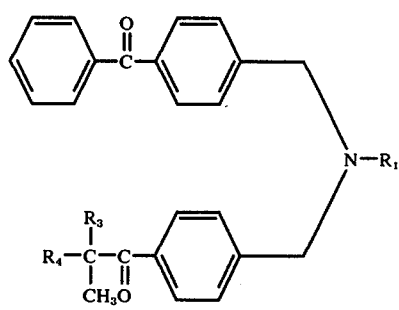

where $R_1$, $R_3$ and $R_4$ are as defined in claim 1, or a pharmaceutically acceptable salt thereof.

3. A compound of the formula

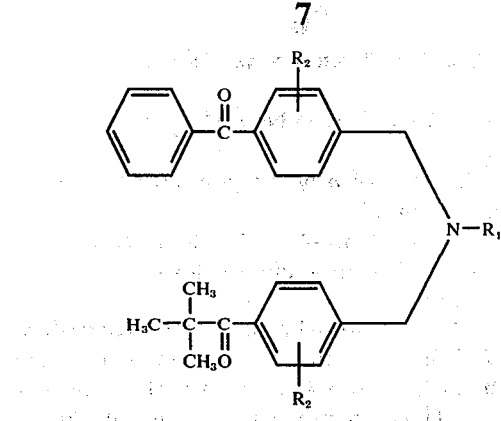

where $R_1$ and $R_2$ are as defined in claim 1, or a pharmaceutically acceptable salt thereof.

4. A compound of the formula

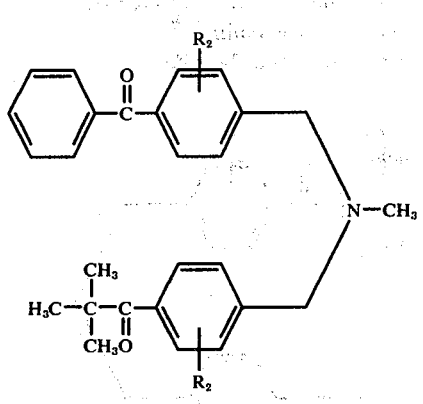

where $R_2$ is as defined in claim 1, or a pharmaceutically acceptable salt thereof.

5. The compound of claim 1 which is 4-{[methyl (p-pivaloylbenzyl)amino]methyl}benzophenone 6. The compound of claim 1 which is 4-{[methyl-p-pivaloylbenzyl)amino]methyl}benzophenone hydrochloride.

7. A compound of the formula

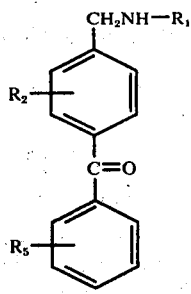

where
$R_1$, $R_2$ and $R_5$ are as defined in claim 1.

8. A pharmaceutical composition comprising an amount of a compound of claim 1 effective in the treatment of lipidemia and a pharmaceutically acceptable diluent or carrier therefor.

9. A method of treating lipidemia which comprises administering to a mammal in need of said treatment a hypolipidemic effective amount of a compound of claim 1 and a pharmaceutically acceptable carrier therefor.

* * * * *